United States Patent
Guo

(10) Patent No.: US 8,633,181 B2
(45) Date of Patent: Jan. 21, 2014

(54) TREATMENT OF CUTANEOUS HEMANGIOMA

(75) Inventor: Suqin Guo, Livingston, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/263,167

(22) PCT Filed: Apr. 9, 2010

(86) PCT No.: PCT/US2010/030566
§ 371 (c)(1),
(2), (4) Date: Oct. 6, 2011

(87) PCT Pub. No.: WO2009/050567
PCT Pub. Date: Apr. 23, 2009

(65) Prior Publication Data
US 2012/0058056 A1    Mar. 8, 2012

Related U.S. Application Data

(60) Provisional application No. 61/212,382, filed on Apr. 9, 2009.

(51) Int. Cl.
*A61K 31/33* (2006.01)
(52) U.S. Cl.
USPC .......................................... 514/183; 514/912
(58) Field of Classification Search
None
See application file for complete search history.

(56) References Cited

U.S. PATENT DOCUMENTS

| 2003/0232089 A1 | 12/2003 | Singh et al. |
| 2006/0257452 A1 | 11/2006 | Hughes et al. |
| 2008/0305103 A1 | 12/2008 | Saragovi |
| 2010/0273889 A1* | 10/2010 | Leaute-Labreze et al. ... 514/652 |

FOREIGN PATENT DOCUMENTS

WO    2009050567 A2    4/2009

OTHER PUBLICATIONS

Collins English Dictionary—Complete and Unabridged, "Lotion", copyright HarperCollins Publishers 2003, accessed Mar. 8, 2013, <http://www.thefreedictionary.com/p/lotion>, pp. 1.*
Collins English Dictionary—Complete and Unabridged, "solution (chemistry)", copyright HarperCollins Publishers 2003, accessed Mar. 11, 2013, <http://www.thefreedictionary.com/p/Solution%20> pp. 1.*
Uusitalo et al., "Efficacy and systemic side-effects of topical 0.5% timolol aqueous solution and 0.1% timolol hydrogel", Acta Ophthalmologica Scandinavica, 2005, vol. 83, pg. 723-728.*
Leaute-Labreze et al. 'Propranolol for Severe Hemangiomas of Infancy',New England J. Medicine 358;24 pp. 26499-2651 Jun. 12, 2008.

* cited by examiner

*Primary Examiner* — Tracy Vivlemore
*Assistant Examiner* — Monica Shin
(74) *Attorney, Agent, or Firm* — Fox Rothschild LLP

(57) ABSTRACT

This invention concerns a method of treating hemangiomas with a beta blocker by applying the beta blocker onto the hemangiomas directly. The invention also concerns a combination therapy by using a beta blocker along with a corticosteroid or an alpha adrenergic receptor agonist for the treatment of hemangiomas.

3 Claims, No Drawings

TREATMENT OF CUTANEOUS HEMANGIOMA

CROSS REFERENCE TO RELATED APPLICATIONS

This application is the U.S. national phase Application of International Patent Application Serial No. PCT/US10/030566, filed Apr. 9, 2010, which claims the benefit under 35 U.S.C. §119(e) of U.S. Provisional Patent Application Ser. No. 61/212,382, filed Apr. 9, 2009, both of which are incorporated herein by reference in their entireties.

FIELD OF THE INVENTION

This invention relates to a method to treat hemangiomas, more particularly hemangiomas on the face, more particularly on the eyelid, with a beta blocker, or its combination with an alpha adrenergic receptor agonist.

BACKGROUND OF THE INVENTION

Hemangioma of the skin can occur on the eyelids, face, arms, legs, or any other parts of the body. It can not only be cosmetically disfiguring and psychologically disturbing, but can also cause functional disability, e.g., blindness, if it occurs on the places such as eyelids.

Current available treatments include corticosteroids (oral or injection), laser or surgery. Most recently, systemic use of propranolol was reported to successfully treat severe capillary hemangioma in infants. Most of these treatments are invasive and involve significant adverse effects, including severe ones such as scarring and/or discoloration of the skin, bleeding of surgical wounds, and respiratory or heart failures.

Capillary hemangioma is the most common benign tumor of the eyelid/orbit in children and affects up to 2% of infants, with a female to male ratio of 3:2. (Peralta, R. J. and Glavas, I. P., *EyeNet,* 2009, 35-37). Capillary hemangioma on the eyelids or face affects over 1.7 million children in USA and over 10 million children worldwide. If it is not treated promptly, it could cause irreversible blindness. The incidence of cutaneous hemangioma is much higher across all ages. Over millions of people can be affected. Cutaneous hemangioma can occur throughout human body and cause physically disfiguring and psychologically disturbing lesions in all age groups affected. It can also cause severe disabilities, such as blindness, in young children.

Systemic or intralesional corticosteroids are commonly used as first line treatment. Alternative treatments include laser photocoagulation, surgical excision and immunomodulators (cyclophosphamide and interferon alfa 2-a, usually reserved for life- or sight-threatening lesions due to their serious side effects).

Most of the treatments reported are associated with complications. Surgical excision is difficult due to the potential for hemorrhage. Immunomodulators have severe systemic adverse effects, for example, myelosuppression and hepatotoxicity for cyclophosphamide, and neurotoxicity (spastic displagia) for interferon alfa-2a.

Even the first-line treatments (i.e., oral or injectable corticosteroids) involve systemic complications. Side effects of systemic corticosteroids include increased risk of hypertension, adrenal cortical insufficiency, growth delay, immunosuppression, gastrointestinal bleeding, diabetes mellitus, weight gain, and behavioral changes. Intralesional corticosteroid injection can cause local complications, including dystrophic periocular calcifications, skin hypopigmentation, fat atrophy, eyelid necrosis (disfiguring), central retinal artery occlusion (sudden blindness), and adrenal suppression (growth retardation in children).

In addition to the side effects, all the currently available treatment options require significant time and effort of both physicians and patients. Clinical physicians have to initiate the treatments and monitor the patients very closely during therapy due to the possibility of severe systemic complications.

More recently, a systemic application of propranolol was reported to successfully treat severe hemangioma of infants. (Léauté-Labrèze, C. et al., *New Engl. J. Med.,* 2008, 358:2649-2651). Significant shrinkage of the hemangioma occurred by about 24 hours after the initiation of systemic propranolol. Propranolol is a nonselective beta1 and beta2 adrenergic receptor blocker used to treat patients with heart diseases and hypertension. The mechanism by which propranolol reduces hemangioma is unclear. It is proposed that propranolol's beta2-mediated vasoconstrictive effect reduces expression of vascular endothelial growth factor (VEGF) and basic fibroblast growth factor (bFGF) genes, which are the two crucial proangiogenic factors involved in the growth (involution) phase of hemangiomas. During the involution phase, both vascular endothelial and interstitial cells are actively dividing.

However, oral application of propranolol, as suggested by the study, can cause severe systemic complications, including bronchospasm, vasospasm, systemic lupus erythematosus, heart block, severe bradycardia, hypotension, and congestive heart failure. (Léauté-Labrèze, C. et al., *New Engl. J. Med.,* 2008, 358:2649-2651). Thus, there remains a need for effective treatments that do not have severe or life-threatening side effects.

SUMMARY OF THE INVENTION

The present invention fulfills the foregoing need by providing a new method to treat cutaneous hemangioma by applying a topical nonselective beta-blocker with strong beta2 antagonist activity directly onto the hemangioma of a human body. The beta-blocker can be applied in the form of a solution, aerosol, cream, or patch, or any other suitable equivalents. The method has proven to be effective in the treatment of capillary hemangioma on the eyelids of a child. The method should also be applicable to the treatment of hemangiomas that occur on any other areas, such as face, arms, and legs, of to a patient in any other age groups.

In one aspect, the present invention provides a method of treating hemangioma in a patient, comprising administering to the patient a topical formulation applied to said hemangioma and comprising a beta-blocker, or a pharmaceutically acceptable salt thereof in an amount effective to reduce the size of the hemangioma.

In another aspect, the present invention provides a pharmaceutical composition, comprising a beta-adrenergic receptor blocker or inhibitor and an alpha-adrenergic receptor agonist, or pharmaceutically acceptable salt(s) thereof in a pharmaceutical carrier for topical application.

In another aspect, the present invention provides a method of treating hemangioma in a patient, comprising administering to the patient by topical application to said hemangioma a composition according to any of the embodiments in the second aspect of the present invention described above in an amount effective to reduce the size of the hemangioma.

In another aspect, the present invention provides a pharmaceutical composition, comprising a beta-adrenergic receptor blocker or inhibitor and a corticosteroid, or pharmaceutically acceptable salt(s) thereof in a pharmaceutical carrier for topical application.

In another aspect, the present invention provides a method of treating hemangioma in a patient, comprising administering to the patient by topical application to said hemangioma a composition according to any of the embodiments in the fifth aspect of the present invention in an amount effective to reduce the size of said hemangioma.

In yet another aspect, the present invention provides the use of a beta blocker in the manufacture of a pharmaceutical composition for topical application to a hemangioma, wherein the amount of said beta blocker in said composition is effective to reduce the size of said hemangioma.

The advantages of using topical beta blocker to treat cutaneous hemangioma by directly applying the medication on the lesion include, but are not limited to, (1) more effective treatment, (2) safety, (3) simple application method, (4) ease of monitoring; (5) little to no systemic complications, and (6) reduction in doctors' office visits.

Specific preferred embodiments of the present invention are described in the following embodiments and claims.

DETAILED DESCRIPTION OF THE INVENTION

The invention relates to the use of a class of compounds known as beta-blockers for the treatment of hemangioma.

In a first aspect, the present invention provides a method of treating hemangioma in a patient, comprising administering to the patient a topical formulation applied to said hemangioma and comprising a beta-blocker, or a pharmaceutically acceptable salt thereof in an amount effective to reduce the size of the hemangioma.

In one embodiment of the first aspect, the present invention provides a method of treating hemangioma in a patient, comprising administering to the patient a topical formulation applied to said hemangioma and comprising a beta-blocker selected from propranolol, timolol, betaxolol, nadolol, alprenolol, carteolol, levobunolol, mepindolol, metipranolol, oxprenolol, penbutolol, pindolol, and sotalol, or a pharmaceutically acceptable salt thereof in an amount effective to reduce the size of the hemangioma.

In another embodiment of the first aspect, the present invention provides a method of treating hemangioma in a patient, comprising administering to the patient a topical formulation applied to said hemangioma and comprising a beta-blocker selected from propranolol and timolol, or a pharmaceutically acceptable salt thereof in an amount effective to reduce the size of the hemangioma.

In another embodiment of the first aspect, the present invention provides a method of treating hemangioma in a patient, comprising administering to the patient a topical formulation applied to said hemangioma and comprising a beta-blocker, or a pharmaceutically acceptable salt thereof in an amount effective to reduce the size of the hemangioma, wherein said treatment is repeated periodically.

In another embodiment of the first aspect, the present invention provides a method of treating hemangioma in a patient, comprising administering to the patient a topical formulation applied to said hemangioma and comprising a beta-blocker, or a pharmaceutically acceptable salt thereof in an amount effective to reduce the size of the hemangioma, wherein the topical formulation is administered in a form of solution drops, ointment, cream, spray, aerosol, or transdermal patch.

In another embodiment of the first aspect, the present invention provides a method of treating hemangioma in a patient, comprising administering to the patient a topical formulation applied to said hemangioma and comprising a beta-blocker, or a pharmaceutically acceptable salt thereof in an amount effective to reduce the size of the hemangioma, wherein the topical formulation is administered in a form of solution drops, ointment, cream, spray, aerosol, or transdermal patch.

In a second aspect, the present invention provides a pharmaceutical composition, comprising a beta-adrenergic receptor blocker or inhibitor and an alpha-adrenergic receptor agonist, or pharmaceutically acceptable salt(s) thereof in a pharmaceutical carrier for topical application.

In one embodiment of the second aspect, the present invention provides a pharmaceutical composition, comprising a beta-adrenergic receptor blocker or inhibitor and an alpha-adrenergic receptor agonist, or pharmaceutically acceptable salt(s) thereof in a pharmaceutical carrier for topical application, wherein the beta-adrenergic receptor blocker is selected from propranolol, timolol, betaxolol, nadolol, alprenolol, carteolol, levobunolol, mepindolol, metipranolol, oxprenolol, penbutolol, pindolol, and sotalol.

In another embodiment of the second aspect, the present invention provides a pharmaceutical composition, comprising a beta-adrenergic receptor blocker or inhibitor and an alpha-adrenergic receptor agonist, or pharmaceutically acceptable salt(s) thereof in a pharmaceutical carrier for topical application, wherein the beta-adrenergic receptor blocker is propranolol or timolol.

In another embodiment of the second aspect, the present invention provides a pharmaceutical composition, comprising a beta-adrenergic receptor blocker or inhibitor and an alpha-adrenergic receptor agonist, or pharmaceutically acceptable salt(s) thereof in a pharmaceutical carrier for topical application, wherein the alpha-adrenergic receptor agonist is an alpha1-agonist or an alpha2-agonist.

In another embodiment of the second aspect, the present invention provides a pharmaceutical composition, comprising a beta-adrenergic receptor blocker or inhibitor and an alpha1-adrenergic receptor agonists selected from methoxamine, methylnorepinephrine, oxymetazoline, and phenylephrine, or pharmaceutically acceptable salt(s) thereof in a pharmaceutical carrier for topical application.

In another embodiment of the second aspect, the present invention provides a pharmaceutical composition, comprising a beta-adrenergic receptor blocker or inhibitor and an alpha2-adrenergic receptor agonists selected from clonidine, guanfacine, guanabenz, guanoxabenz, guanethidine, xylazine, and methyldopa, or pharmaceutically acceptable salt(s) thereof in a pharmaceutical carrier for topical application.

In a third aspect, the present invention provides a method of treating hemangioma in a patient, comprising administering to the patient by topical application to said hemangioma a composition according to any of the embodiments in the second aspect of the present invention described above in an amount effective to reduce the size of the hemangioma.

In one embodiment of the third aspect, the present invention provides a method of treating hemangioma in a patient, comprising administering to the patient by topical application to said hemangioma a composition according to any of the embodiments in the second aspect of the invention in an amount effective to reduce the size of the hemangioma, wherein said treatment is repeated periodically.

In one embodiment of the third aspect, the present invention provides a method of treating hemangioma in a patient, comprising administering to the patient by topical application to said hemangioma a composition according to any of the embodiments in the second aspect of the invention in an amount effective to reduce the size of the hemangioma, wherein the topical formulation is administered in a form of solution drops, ointment, cream, spray, aerosol, or transdermal patch.

In one embodiment of the third aspect, the present invention provides a method of treating hemangioma in a patient, comprising administering to the patient by topical application to said hemangioma a composition according to any of the embodiments in the second aspect of the invention in an amount effective to reduce the size of the hemangioma, wherein the topical formulation is administered in a form of solution drops, ointment, cream, spray, aerosol, or transdermal patch.

In a fourth aspect, the present invention provides a pharmaceutical composition, comprising a beta-adrenergic receptor blocker or inhibitor and a corticosteroid, or pharmaceutically acceptable salt(s) thereof in a pharmaceutical carrier for topical application.

In one embodiment of the fourth aspect, the present invention provides a pharmaceutical composition, comprising a beta-adrenergic receptor blocker or inhibitor and a corticosteroid, or pharmaceutically acceptable salt(s) thereof in a pharmaceutical carrier for topical application, wherein the beta-blocker is selected from propranolol, timolol, betaxolol, nadolol, alprenolol, carteolol, levobunolol, mepindolol, metipranolol, oxprenolol, penbutolol, pindolol, and sotalol.

In one embodiment of the fourth aspect, the present invention provides a pharmaceutical composition, comprising a beta-adrenergic receptor blocker or inhibitor and a corticosteroid, or pharmaceutically acceptable salt(s) thereof in a pharmaceutical carrier for topical application, wherein the beta-blocker is propranolol or timolol.

In a fifth aspect, the present invention provides a method of treating hemangioma in a patient, comprising administering to the patient by topical application to said hemangioma a composition according to any of the embodiments in the fifth aspect of the present invention in an amount effective to reduce the size of said hemangioma.

In one embodiment of the fifth aspect, the present invention provides a method of treating hemangioma in a patient, comprising administering to the patient by topoical application to said hemangioma a composition according to any of the embodiments in the fourth aspect of the present invention described above in an amount effective to reduce the size of said hemangioma, wherein said treatment is repeated periodically.

In one embodiment of the fifth aspect, the present invention provides a method of treating hemangioma in a patient, comprising administering to the patient by topical application to said hemangioma a composition according to any of the embodiments in the fourth aspect of the present invention described above in an amount effective to reduce the size of said hemangioma, wherein the topical formulation is administered in a form of solution drops, ointment, cream, spray, aerosol, or transdermal patch.

In yet another aspect, the present invention provides the use of a beta blocker in the manufacture of a pharmaceutical composition for topical application to a hemangioma, wherein the amount of said beta blocker in said composition is effective to reduce the size of said hemangioma.

In any of the above embodiments, the concentrations of the beta-blocker, alpha-agonist, and corticosteroid in said compositions can each independently be in a range from about 0.01% to about 99.99% by weight. However, when a composition comprises a plurality of these agents, it is the sum of their concentrations combined that can be in the above range.

The formulations of the invention are those known in the art for topical or transdermal applications, including but not limited to solutions, aerosols, creams, gels, and patches.

As used herein, the term "therapeutically effective amount" refers to the amount of a compound sufficient to effect beneficial or desired results. A therapeutically effective amount can be administered in one or more administrations, applications or dosages and is not intended to be limited to a particular formulation or administration route.

As used herein, the term "co-administration" or "co-administered" refers to the administration of at least two agent(s) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions, and various types of wetting agents. The compositions also can include stabilizers and preservatives.

As used herein, the term "pharmaceutically acceptable salt" refers to any pharmaceutically acceptable salt (e.g., acid or base) of a compound of the present invention, which, upon administration to a subject, is capable of providing a compound of this invention or an active metabolite or residue thereof. As is known to those of skill in the art, "salts" of the compounds of the present invention may be derived from inorganic or organic acids or bases.

Examples of acid addition salts include, but are not limited to, hydrochloride, hydrobromide, hydroiodide, sulfate, phosphate, acetate, propionate, butyrate, benzoate, benzenesulfonate, 2-naphthalenesulfonate, methanesulfonate, ethanesulfonate, citrate, lactate, maleate, nicotinate, oxalate, picrate, pivalate, succinate, and tartrate salts, or the like. Examples of base addition salts include, but are not limited to, alkali metal cation salts, alkaline earth metal salts, ammonium or tetraalkylammonium salts, and so on.

Pharmaceutical compositions for topical administration according to the present invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents.

For treatments of hemangioma around the eye or on the face, the formulations may preferably be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

In some embodiments, a hydrophilic emulsifier may be preferably included together with a lipophilic emulsifier so as to act as a stabilizer. Emulsion stabilizers suitable for use in the formulation of the present invention include, but are not limited to, Tween 60, Span 80, cetostearyl alcohol, myristyl alcohol, glyceryl monostearate, and sodium lauryl sulfate.

The choice of suitable oils or fats for the formulation is based on achieving the desired properties. Straight or branched chain, mono- or dibasic alkyl esters, such as diisoadipate, isocetyl stearate, isopropyl myristate, isopropyl palmitate, decyl oleate, butyl stearate, 2-ethylhexyl palmitate, propylene glycol diester of coconut fatty acids, or a blend of branched chain esters known as Crodamol CAP may be used. These may be used alone or in combination depending on the properties required. Alternatively, high melting point lipids such as white soft paraffin and/or liquid paraffin or other mineral oils can be used.

In some preferred embodiments, the topical formulations include a material that would enhance absorption or penetration of the active agent(s) through the skin or other affected areas.

Pharmaceutical formulations adapted for topical administrations to the eye itself include eye drops wherein the active ingredient is dissolved or suspended in a suitable carrier, especially an aqueous solvent.

The following is an illustrative example of the present invention, in which a four-month-old child having a large and visually threatening capillary hemangioma on the left upper eyelid was treated by application of a topical beta-blocker solution, resulting in a prompt and significant reduction of the hemangioma. The capillary hemangioma is decreased in size, thickness, and color within 3-4 weeks of the treatment. This treatment permitted safe and effective clearance of the child's visual axis. No local or systemic side effects were noted. While the mechanism by which beta blockade improves hemangioma is unclear, beta2-mediated vasoconstrictive effects may contribute to the therapeutic results of the present invention.

EXAMPLE

A four month-old girl had a large capillary hemangioma on her left upper eyelid, which induced mechanical ptosis and covered her left pupil. Her right eye seemed to follow and fixate targets well, while the left eye was slow to fixate. She was orthophoric in primary position with full duction and version in all fields of gaze without nystagmus. Her ocular exam showed normal anterior segment, normal optic nerve and retina in both eyes. Her cycloplegic retinoscopy showed +3.50-1.50×180 in the right eye and +4.50-3.75×180 in the left eye. Over two diopters of astigmatism induced anisometropia in the left eye. A 0.5% timolol maleate Ophthalmic solution (Bausch & Lomb Incorporated, Tempa, Fla. 33637) was used to treat the hemangioma in a form of liquid drops twice daily, with one drop into the left eye and another drop onto the surface of the hemangioma with a gentle spread by a finger. After four weeks of topical application, the child was re-examined. The hemangioma was significantly reduced in size and thickness and faded in color. The mechanical ptosis improved and the pupil was spared. The child was able to follow and fixate very well in the left eye. After ten weeks of the topical treatment, retinoscopy showed decreased astigmatism in the left eye, and intraocular pressure remained normal in both eyes.

The foregoing example and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

What is claimed is:

1. A method of treating a cutaneous capillary hemangioma of an eye lid or orbit that is inducing mechanical ptosis in an infant patient, comprising applying a topical timolol formulation to said eye and said hemangioma, or a pharmaceutically acceptable salt thereof, in an amount effective to reduce the size of the hemangioma, periodically until the visual axis of said infant is cleared and the mechanical ptosis improves, wherein said effective amount maintains normal intraocular pressure of said eye and produces little to no local side effects or systemic complications.

2. The method according to claim 1, wherein the topical timolol formulation is applied in a form of solution drops, gel, ointment, cream, spray, aerosol, or transdermal patch.

3. The method according to claim 1, wherein the topical timolol formulation is a timolol solution.

* * * * *